(12) United States Patent
Canaani et al.

(10) Patent No.: US 6,569,623 B1
(45) Date of Patent: May 27, 2003

(54) GENETIC SCREENING METHODS

(75) Inventors: Dan Canaani, Ra'Anana (IL); Yoram Oron, Tel Aviv (IL); Arnold Simons, Carcur (IL); Naomi Dafni, Keisaria (IL); Iris Dotan, Tel Aviv (IL)

(73) Assignee: Ramot University Authority for Applied Research & Industrial Development Ltd., Ramat Aviv (IL)

( * ) Notice: Subject to any disclaimer, the term of this patent is extended or adjusted under 35 U.S.C. 154(b) by 0 days.

(21) Appl. No.: 09/391,444

(22) Filed: Sep. 8, 1999

(51) Int. Cl.[7] ................... C12Q 1/68; C12N 15/74; C07H 21/02

(52) U.S. Cl. ................. 435/6; 435/471; 435/476; 435/320.1; 435/DIG. 1; 435/DIG. 2; 435/DIG. 3; 435/DIG. 9; 435/DIG. 14; 536/23.1; 536/25.32

(58) Field of Search .............. 435/6, 29, 320.1, 435/481, DIG. 1, DIG. 2, DIG. 3, DIG. 9, DIG. 14, 476; 530/350; 536/23.5, 23.1, 25.32, 23.4, 18.7

(56) References Cited

U.S. PATENT DOCUMENTS 5,882,880 A * 3/1999 Canaani ............... 435/29
6,057,111 A * 5/2000 Deiss et al. ............. 435/6

FOREIGN PATENT DOCUMENTS

WO   WO 99/24603   5/1999

OTHER PUBLICATIONS

Deiss et al., Science, vol. 252., pp. 117–120, Apr. 5, 1991.*
Wade–Martins et al., Nucleic Acid Research., vol. 27, No. 7, pp. 1674–1682, 1999.*
Van Meir et al., Single cell monitoring of growth arrest and morphological changes induced by transfer of wild–type p53 alleles to glioblastoma cells—Proc. Natl. Acad. Sci., vol. 92, 1995, pp. 1008–1012, XP–002157214, XP–002157217. XP–002157217.
Carmenisch et al., A polyoma–based episomal vector efficiently expresses exogenous genes in mouse embroyonic stem cells, Nucleic Acids. Res., vol. 24, No. 19, 1996, pp. 3707–3713, XP–002157215.
Galli et al., DNA Replication and Order of Cell Cycle Events: A Role for Protein Isoprenylation?, Biol. Chem., vol. 378, 1997, pp. 963–973, XP–00215216.
Calos, The potential of extrachromosomal replicating vectors for gene therapy, TIG Nov. 1996, vol. 12, No. 11, pp. 463–466, XP–418563A.
Koshland et al., Genetic Analysis of the Mitotic Transmission of Minichromosomes, Cell, vol. 40, 1985, pp. 393–403.
Doyle et al., Genetic approaches to nuclear pore structure and function, TIG Jun. 1995, vol. 11, No. 6, pp. 235–241.
Bender et al., Use of a Screen for Synthetic Lethal and Multicopy Suppressee Mutants to Identify Two Genes Involved in Morphogenesis in Saccharamyces cerevisiae, Molecular and Cellular Biology, 3/91, vol. 11, No. 3 pp. 1295–1305.

* cited by examiner

*Primary Examiner*—Padmashri Ponnaluri
(74) *Attorney, Agent, or Firm*—Eitan, Pearl, Latzer & Cohen Zedek, LLP.

(57) ABSTRACT

A screening method which applies the principle of synthetic lethality to a gene of interest in non-yeast eukaryotic cells. The method may be used to screen either a chemical library in order to identify a molecule having a gene-specific lethal property in the cells, or to screen a group of DNA molecules in order to identify among them one or more modulators of gene function which are synergistically lethal to the cells together with an incapacitated gene of interest. Also described are episomal survival plasmids and kits which may be used with the method.

9 Claims, 9 Drawing Sheets

GENETIC SCREENING METHODS

FIELD OF THE INVENTION

This invention relates to genetic screening methods useful in isolating genes and identifying unknown functions of genes or unknown functional links between genes as well as in identifying molecules having gene-specific lethal properties.

BACKGROUND OF THE INVENTION

The following publications may be relevant to the invention, and are referred to in the specification by number:

1. Bender and J. R. Pringle, *Mol. Cell. Biol.* 11, 1295 (1991);
2. V. Doye and E. C. Hurt, *Trends Genetics* 11, 235 (1995);
3. Koshland, D. et al, Cell 40,393 (1985).

With continued progress in the Human Genome Project as well as the initiation of the Mouse/Rat Genome Projects, and the sequencing of the majority of the human cDNAs, the elucidation of gene function has become a major priority. High throughput screening methods are required in order to determine the functions of large numbers of genes in an efficient manner.

Screening methods are also required for discovering novel gene-specific drugs. In the search for such drugs, it would be advantageous to be able to elucidate the interaction between specific chemical reagents and one or more genes in a high throughput format. This is particularly relevant with respect to cancer drugs.

A synthetic or synergistic lethality screening method has previously been described in yeast cells (1,2). The essence of this screen in yeast, is the ability to identify nonallelic and nonessential mutation/s that are lethal in combination with a nonessential mutation in a gene of interest (i.e. synthetic lethality). A wild-type copy of the gene of interest, on an episomal plasmid, is introduced into cells which are null for expression of this gene. Random chemical mutagenesis of the entire yeast genome within these cells may inactivate a gene which is synthetically lethal with the gene of interest. Under these conditions, retention of the episomal plasmid, which is otherwise spontaneously lost, and expression of the gene of interest become essential for survival (i.e. survival plasmid). Plasmid loss or retention is detected by changes in colony pigmentation, due to the presence on the plasmid of a wild-type gene whose product is essential for red pigment accumulation (3). This genetic method is very powerful as it can reveal not only interactions between gene products with direct physical contacts, but also interactions along the same or parallel pathways.

A synthetic lethality screen in non-yeast eukaryotic cells in general and in human cells in particular, has not yet been described.

SUMMARY OF THE INVENTION

In an effort to expand the arsenal of genetic tools which can be applied to other eukaryotic biological systems, it has now been discovered that the concept of the yeast synthetic lethality screen can be applied to non-yeast eukaryotic cells, particularly to mammalian cells and most particularly to human cells.

An object of the present invention is to provide a screening method useful in identifying molecules having gene-specific cell-lethal properties.

A further object of the present invention is to provide a screening method useful in isolating genes and identifying unknown functions of genes or unknown functional links between genes.

In a first aspect of the invention, there is provided a method for screening a chemical library comprising a plurality of molecule types in non-yeast eukaryotic cells having a genome, in order to identify a molecule type having a gene-specific lethal property in the cell, the genome comprising a gene of interest which carries a non-lethal mutation therein.

The method comprises the following steps:
(a) transfecting a first reporter gene into the cells, and selecting clones stably expressing the reporter gene;
(b) introducing into the cells an episome comprising a functioning copy of the gene of interest, a second reporter gene, a dominant selectable marker, an origin of DNA replication and a nuclear antigen gene essential for replication of the episome within the cells, wherein the episome is spontaneously lost from the cells, and growing the cells in the presence of a selection compound which selects for the dominant selectable marker;
(c) selecting cell clones stably expressing the second reporter gene and the functioning copy of the gene of interest;
(d) seeding of the cells into a plurality of cell chambers and removing the selection compound;
(e) adding a molecule type of the chemical library to each of the plurality of cell chambers, measuring expression of the first and second reporter genes in the chambers, and calculating the ratio of the measured expressions, thereby indicating retention of the episome; and
(f) identifying a cell chamber in which the episome is retained, thus identifying a molecule type having a gene-specific lethal property in the cell.

In this aspect of the invention, chemical reagent induced synthetic lethality (i.e. chemical synthetic lethality) identifies biochemical inhibitors or drugs whose lethal effect is dependent on the full or partial inactivation of a specific gene (i.e. gene of interest) within its cellular milieu.

In an alternate embodiment of this aspect of the invention, there is provided a method for screening a chemical library comprising a plurality of molecule types in non-yeast eukaryotic cells having a genome, in order to identify a molecule type having a gene-specific lethal property in the cell, the genome comprising a wild-type gene of interest.

The method comprises the following steps:
(a) transfecting a first reporter gene into the cells, and selecting clones stably expressing the reporter gene;
(b) introducing into the cells an episome comprising a dominant-negative mutant of the gene of interest, a second reporter gene, a dominant selectable marker, an origin of DNA replication and a nuclear antigen gene essential for replication of the episome within the cells, wherein the episome is spontaneously lost from the cells, and growing the cells in the presence of a selection compound which selects for the dominant selectable marker;
(c) selecting cell clones stably expressing the second reporter gene and the dominant-negative mutant of the gene of interest;
(d) seeding of the cells into a plurality of cell chambers and removing the selection compound;
(e) adding a molecule type of the chemical library to each of the plurality of cell chambers, measuring expression of the first and second reporter genes in the chambers, and calculating the ratio of the measured expressions, thereby indicating retention of the episome; and (f) identifying a cell chamber in which the episome is retained, thus identifying a molecule type having a gene-specific lethal property in the cell.

In a second aspect of the invention, there is provided a method for screening a collection of DNA molecules selected from the group consisting of antisense cDNA, truncated cDNA, full-length cDNA and genomic DNA, in order to identify from among them one or more modulators of gene function which are synergistically lethal to a non-yeast eukaryotic cell together with an incapacitated gene of interest, the cell having a genome which comprises the incapacitated gene of interest.

The method of this aspect of the invention comprises the following steps:

(a) transfecting a first reporter gene into the cell, and selecting clones stably expressing the reporter gene;

(b) introducing into the cells an episome comprising a functioning copy of the gene of interest, a second reporter gene, a first dominant selectable marker, an origin of DNA replication and a nuclear antigen gene essential for replication of the episome within the cells, wherein the episome is spontaneously lost from the cells, and growing the cells in the presence of a selection compound which selects for the first dominant selectable marker;

(c) selecting cell clones stably expressing the second reporter gene and the functioning copy of the gene of interest;

(d) incorporating each of the DNA molecules into vector vehicles containing a second dominant selectable marker gene;

(e) transfecting the cells with the vector vehicles so that each transfected cell contains on the average approximately one to several of the molecules, and allowing expression of the molecules in the cells;

(f) seeding the transfected cells into a plurality of cell chambers under conditions of one stably transfected cell or less per chamber, and initiating conditions for selection of the second dominant marker, while removing the selection compound for the first dominant selectable marker;

(g) measuring expression of the first and second reporter genes in the chambers, and calculating the ratio of the measured expressions, thereby indicating retention of the episome; and (h) identifying a cell chamber in which the episome is retained, thus identifying a DNA molecule which is a modulator of gene function.

In a further embodiment of this aspect of the invention, there is provided a method for screening a collection of DNA molecules selected from the group consisting of antisense cDNA, truncated cDNA, full-length cDNA and genomic DNA, in order to identify among them one or more modulators of gene function which are synergistically lethal to a non-yeast eukaryotic cell, the cell having a genome which comprises a wild-type gene of interest.

The method of this embodiment comprises the following steps:

(a) transfecting a first reporter gene into the cell, and selecting clones stably expressing the reporter gene;

(b) introducing into the cells an episome comprising a dominant-negative mutant of the gene of interest, a second reporter gene, a first dominant selectable marker, an origin of DNA replication and a nuclear antigen gene essential for replication of the episome within the cells, wherein the episome is spontaneously lost from the cells, and growing the cells in the presence of a selection compound which selects for the first dominant selectable marker;

(c) selecting cell clones stably expressing the second reporter gene and the dominant-negative mutant of the gene of interest;

(d) incorporating each of the DNA molecules into vector vehicles containing a second dominant selectable marker gene;

(e) transfecting the cells with the vector vehicles so that each transfected cell contains on the average approximately one to several of the molecules, and allowing expression of the molecules in the cells;

(f) seeding the transfected cells into a plurality of cell chambers under conditions of one stably transfected cell or less per chamber, and initiating conditions for selection of the second dominant marker, while removing the selection compound for the first dominant selectable marker;

(g) measuring expression of the first and second reporter genes in the chambers, and calculating the ratio of the measured expressions, thereby indicating retention of the episome; and (h) identifying a cell chamber in which the episome is retained, thus identifying a DNA molecule which is a modulator of gene function.

In this aspect of the invention, synthetic lethality imposed by either a GSE (defined below) or by an overexpressed full-length cDNA (i.e. genetic synthetic lethality) identifies gene function or functional links between genes.

The following terms used in the present specification have the indicated definitions:

non-essential gene—a gene whose function is non-essential to the viability of the cell, either because it is dispensable for cell metabolism or due to the existence of one or more other genes which functionally overlap with it.

non-lethal mutation—a mutation within a non-essential gene or a defect within an essential gene which is partial and thus leaves the cell viable.

gene of interest—a specific gene which is either non-essential for viability or an essential gene carrying a non-lethal mutation. Its function may be known or unknown.

synthetic or synergistic lethality—a lethal cell phenotype which is the result of either the synergistic incapacitation of two (or more) genes, or due to the overexpression of one gene on the background of the incapacitation of the gene of interest. Either one of these two conditions may also require the overexpression and/or underexpression of other gene(s). The incapacitation of activity may be full or only partial. The incapacitation may be as a result of a resident mutation, or due to an externally inserted element, such as a truncated cDNA, an antisense cDNA molecule or a chemical reagent.

Episomal survival plasmid—a gene vehicle/vector which carries either a functioning copy or a dominant-negative mutant of a gene of interest. The plasmid is not incorporated into the genome of the cell, and yet can autonomously replicate within the cell (i.e. an episome). The plasmid is spontaneously gradually lost from the cell population.

genetic suppressor element (GSE)—a nucleic acid capable of suppressing genetic expression in a dominant-negative fashion. Examples of GSEs are antisense cDNA, truncated sense cDNA, and other forms of mutated DNA.

modulators of gene expression—a group of DNA molecules which affect gene expression of the host cells. These DNA molecules are either GSEs or overexpressed wild-type genes.

chemical library—a group of different chemical reagents which may comprise synthetic as well as natural compounds. Each of the different types of reagents may be referred to at times as 'molecule types'. This definition also includes, but is not limited to, synthetic antisense DNA oligonucleotides which may also be modified (phosphorothioate antisense oligodeoxynucleotides, chimeric oligodeoxynucleotides, etc.).

The method of the invention is based on the screening of a cell population for either loss of gene function or gene overexpression resulting in lethality. The survival plasmid carries the genetic information which is necessary for cell survival under the specific conditions of the imposed synthetic lethality. This results in a strong selective advantage for retaining the episomal survival plasmid which would otherwise be lost from the cell. In this manner, the phenotype of lethality may be identified by the maintenance of the plasmid in an otherwise non-viable cell.

Synthetic lethality is dependent on two independent events of gene incapacitation, or a combination of the incapacitation of the gene of interest, and overexpression of the other gene in its non-mutated form. The gene incapacitation may be either by genetic means or by an external specific chemical inhibitor. Thus, if the nature of one of the events is known, the nature of the other event can be surmised as being overlapping, complementing or antagonizing the first event. In this way, an unknown function may be identified.

The method of the invention differs from the synthetic lethality screen previously described in yeast in the following respects:

(1) Synthetic lethality as disclosed in yeast is recognized by the visible color of yeast colonies grown on agar within petri dishes. The majority of colonies exhibit the appearance of white sectors within red colonies, while a synthetic lethal condition prevents the appearance of white sectors in a primarily red colony. The accumulation of red pigment is enabled by the reporter gene acting together with other genes.

In contrast, the method of the invention involves the seeding of human/mammalian cells into microtiter plates, and the periodic measurement in a fluorescent plate reader of the double-label fluorescent ratio of two fluorescent proteins. Retention over time of a high ratio in the readings of a fluorescent variant encoded by the survival plasmid to a second fluorescent variant produced from a chromosomally integrated gene, indicates selection for maintenance of the survival plasmid and thus a synthetic lethality condition. The fluorescence is a direct product of the reporter gene.

(2) Synthetic lethality is imposed in yeast by randomly mutagenizing the whole yeast genome with a chemical mutagen, thus leading to random gene inactivation. In contrast, in the present invention, synthetic lethality is achieved by either a chemical inhibitor (chemical synthetic lethality) or a genetic incapacitation (genetic synthetic lethality). The latter involves overexpressing sense cDNA libraries or GSE libraries, either one of which is incorporated into episomal plasmids (J. L. Yates, N. Warren and B. Sugden, Nature 313, 812 (1985); L. P. Deiss and A. Kimchi, Science 252, 117 (1991)), retroviral vectors (A. V. Gudkov et al., Proc. Natl. Acad. Sci. USA 90, 3231 (1993)), chimeric transposable elements (Z. Ivics et al, Cell 91,501 (1997)) or episomal viral vectors.

(3) Identification of the gene which is synthetic lethal with the gene of interest is performed in yeast by first isolating those colonies in which the red pigment was maintained and no white sectors appear. Those colonies putatively harbor a chromosomally mutated gene which is synthetic lethal with the gene of interest. Those yeast colonies are transfected by a normal yeast genomic library incorporated into a yeast multi-copy plasmid. Those transformants transfected by and expressing a wild-type copy of the chromosomally mutated gene, no longer sustain a synthetic lethality condition, and therefore no longer need to retain the survival plasmid. Those few colonies are recognized by the appearance of white sectors, from which the plasmid DNA is extracted, transformed into bacteria and further analyzed for the identity of the yeast gene insert by standard recombinant DNA methods.

Identification of the genetic element which confers the synthetic lethal phenotype in human/mammalian cells of the present invention, on the other hand, does not require a further transfection with a normal gene/cDNA library. This is because, unlike in the yeast method, gene incapacitation is not achieved by mutagenizing the endogenous resident cell genome but rather by an exogenous DNA element working either in a dominant-negative fashion or by overexpression of a wild-type cDNA. Accordingly, the external genetic element conferring the synthetic lethality is recovered by either one of two approaches, depending on the type of vector/vehicle used: (a) an episomal plasmid, or a chimeric episomal virus are rescued by Hirt supernatant extract mediated bacterial transformation or virus particle purification, respectively; (b) chromosomally integrated GSE or a wild-type sense cDNA library incorporated into either a retroviral vector or a chimeric transposable element, are recovered by PCR on genomic DNA.

The availability of a large number of mutant human cell lines derived from genetic disorders on the one hand, and the ability to employ homologous recombination for gene disruption in somatic human cells on the other, constitutes a large reservoir of recipient cells and genes of interest.

The cells which may be used in the method of the invention are non-yeast eukaryotic cells. Preferably they are human cells, but the same principle may be applied to e.g., rodent cells harboring a survival plasmid with the appropriate replication properties.

The survival plasmid contains a reporter gene so as to enable determination of the presence of the plasmid in the cells. The product of the reporter gene may be any detectable molecule, such as the following biosensors: luciferin (luciferase substrate); aequorin; Fluo-3/acetoxymethyl (esterase substrate); FDG ($\beta$-gal substrate); or CCF2 which is a $\beta$-lactamase substrate [J. E. González and P. A. Negulescu, Curr. Opin. Biotechnol. 9, 624 (1998)]. Preferably, the reporter gene encodes a fluorescent protein whose expression can be distinguished from that of a second fluorescent protein marking the cell number. Non overlapping excitation or emission spectra of the two fluorescent proteins allows for double-label fluorescence measurement.

Accordingly the cells are also made to incorporate in their genome a second reporter gene which indicates the number of cells. By comparing the signals obtained from the two reporter genes, a relative ratio between the number of survival plasmids and the number of cells may be determined.

The methods of the invention may be carried out using conventional systems for growing, scanning and sorting cells, such as microtiter plates, 96-well, 384-well or other high-density microplates, a microplate fluorescent reader, and a fluorescent activated cell sorter (FACS). The methods are especially useful in high throughput screening, where automation allows for the rapid screening of large number of chemicals as well as the full spectrum of mammalian genes and their respective GSEs.

Examples of GSEs are dominant-negative genetic elements such as truncated sense cDNA and antisense cDNA.

The present invention may be used in a number of applications.

The first aspect of the invention should prove advantageous in the search of drugs which synergize with particular gene deficiencies to cause cell lethality. A special application of this aspect would be to look for chemicals which kill either a benign or cancerous cell growth in a defined genetic milieu where the chemical is synthetic lethal with a particular mutant gene.

The second aspect of the invention is useful in identifying human genes whose under or over-expression causes lethality of human cell lines with defined genetic abnormalities. Such genes are obviously potential targets for drugs aimed at eliminating the affected cells/tissue. The application of this approach to human tumor-derived cell lines, is particularly amenable to identification of targets for cancer therapy.

Above and beyond the identification of gene targets of therapeutic interest in defined genetic background, the invention should prove useful as a tool for basic research. In particular, the invention may enable researchers to rapidly screen large sets of gene products for functional interactions and helps define genetic pathways within the cell (2).

The method using rodent cells should be useful as a model for human genetic traits and responses in drug development and disease research. For example, mutant mice generated by either homologous recombination or tagged random mutagenesis, supply a large source of recipient mutated mouse embryo fibroblasts which, together with the methods of the invention, will greatly facilitate research and development of new drugs and therapeutic strategies for human beings.

Also included in the invention are kits for synthetic lethality screening. One such kit in accordance with the first aspect of the invention would preferably include an episomal survival plasmid and an integrating vector, each carrying a reporter gene, for a chemical synthetic lethality screen. A kit in accordance with the second aspect of the invention would preferably include the above genetic elements together with a library of GSEs or sense cDNAs incorporated within an episomal vector.

DETAILED DESCRIPTION OF THE DRAWINGS

In order to understand the invention and to see how it may be carried out in practice, a preferred embodiment will now be described, by way of non-limiting example only, with reference to the accompanying drawings, in which:

(A) The pIS integrating sphGFP vector. (B) The HGPRT-tpzGFP survival plasmid. P-CMV, P-TK and P-RSV indicate the promoters of herpes TK1, CMV and RSV, respectively. IVS represents the rabbit β globin second intron. PA stands for polyadenylation signal. Filled-in arrows indicate open reading frames translated in the transduced human cells. For construction details, see the Methods section.

FIG. 3 shows photographs and fluorescent images of vector transfected cells.

(C–E) HIS4 cells expressing the pIS construct. (F–H) Clone 12 cells that express both the sphGFP from the pIS construct, and tpzGFP from the episomal survival plasmid. Panels C and F are photographs of the phase image. Fluorescent images in panels D, E, F and G were obtained using filter sets that preferentially detect sphGFP (D, G), or tpzGFP (E, H). The Clone 12 cells were maintained in hygromycin B selection to retain the survival plasmid. Microscopic images were captured using an Olympus BX40 microscope with a Sony CCD-Iris color video camera. SphGFP was visualized using a filter block with an excitation bandpass of 340–380 nm. TpzGFP was visualized using a filter block with an excitation bandpass of 450–490 nm.

Cells were maintained in 96 well plates over the entire time period (□), or grown by continuous passaging in 90 mm petri dishes (Δ). Passaged cells were trypsinized and seeded into microplates on the day of reading. Plates were read using a microplate fluorescence reader (see Methods section). Data points show the mean relative fluorescence ratio between tpzGFP and sphGFP, expressed as a percentage of the same ratio measured from cells maintained under hygromycin B selection. All data represent the mean of fluorescence reading from at least 3 wells.

FIG. 5: Cells were maintained in 96 well microplates, hygromycin B was removed and replaced with GATA medium+MPA in serial dilutions starting with 25 μg/ml. Microplates were read after two weeks.

FIG. 6: Cells in 96 well microplates were maintained over the entire time period in either GATA medium+12.5 μg/ml MPA (□) or in GATA medium alone (Δ).

Plate reading and data representation is as in FIG. 4.

DETAILED DESCRIPTION OF A PREFERRED EMBODIMENT

Materials and Methods

A. Construction of Plasmids

The plasmid pIS was constructed by replacing the BamHI fragment encoding CD20 from pCMV-CD20 (kind gift from S. van den Heuvel and E. Harlow) with a blunt-ended HindIII-BamHI fragment containing the coding sequence of sphGFP from the pGFPsph-b [R] vector (Packard Instruments).

The episomal HGPRT-tpzGFP survival plasmid was constructed by first cloning a HindIII-BamHI blunt-ended fragment encoding the tpzGFP and polyadenylation signal from the pGFPtpz-b [R] vector (Packard Instruments) into the HindIII site of pCEP4 (Invitrogen). The coding sequence of HGPRT was cloned into pcDNA3 (Invitrogen) and subsequently removed together with the CMV promoter by digestion with BgIII and BamHI. This fragment was then cloned into the BamHI site of the pCEP4-GFP vector. The final survival plasmid was produced by cloning the KpnI-BamHI fragment of the pCEP4-HGPRT-tpzGFP vector into the KpnI-BamHI site of pREP4 (Invitrogen), such that tpzGFP is under the influence of the RSV promoter.

B. Construction of Monogenic GSE Libraries

The human adenosine phosphoribosyltransferase (APRT) cDNA and the human GMP synthetase cDNA were each amplified by PCR from a human lymphocyte cDNA library. The design of the primers was based on the known cDNA sequence for each. Following amplification, the corresponding PCR segments were isolated, cloned into a KS plasmid, and their identity verified by DNA sequencing. The human APRT cDNA and, independently, the human GMP synthetase cDNA, were digested by partial DNase cleavage into fragments of one hundred to several hundred base pairs. The resulting DNA ends were flushed by Klenow/T4 DNA polymerase and ligated to two DNA adaptors; one carrying three initiator ATG codons and a HindIII recognition sequence, and the other three stop codons and a XhoI restriction site. Both codons were designed to be in all three reading frames. The GSE mixture was amplified by PCR with two of the four primers constituting the adaptors, and digested by HindIII and XhoI. These GSE libraries were then cloned into a pREP9-based episomal vector carrying either the zeocin—or puromycin-resistance genes.

In order to attain a library plasmid encoding zeocin resistance, the zeocin$^R$ coding region together with the bacterial EM-7 promoter were removed from the pVgRXR vector (Invitrogen) by digestion with PstI and SalI. This fragment was blunted with T4 DNA polymerase and ligated to a T4 DNA polymerase blunted pREP9 vector (Invitrogen) digested with RsrII and BglII, creating pREP9zeo. Replacement of the pREP9 neomycin$^R$ coding region with a puromycin$^R$ coding region was carried out as follows. The appropriate fragment from pBSpac was isolated by digesting with HindIII and BamHI followed by blunting with T4 DNA polymerase. This fragment was cloned into pFastBac HTh (Life Technologies) in the EheI site. Following this step, the fragment was removed with RsrII and BamHI and subcloned into pREP9 digested with RsrII and BglII, creating pREP9puro. The HindIII and XhoI digested library fragments were then cloned into the HindIII and XhoI sites located in the multiple cloning site of pREP9zeo or pREP9puro.

C. Expression of Constructs in Cells.

HGPRT-deficient HT1080 fibrosarcoma cells (W. F. Benedict, et al., Cancer Res. 44,3471 (1984)) were maintained in Dulbecco's modified Eagle medium (DMEM) supplemented with 10% fetal calf serum (FCS) and 4 mM L-glutamine. This cell line has a generation time of about 24 hours, and a pseudo diploid chromosomal karyotype. Transfections were carried out using the calcium phosphate precipitation technique as previously described (T. Teitz et al., Proc. Natl Acad Sci. USA 84, 8801 (1987)).

For pIS, selection in G418 (Calbiochem) was carried out at 400 µg/ml, while maintenance was at 50 µg/ml. For the HGPRT-tpzGFP survival plasmid, selection in HYGROMYCIN B (Sigma) was at 150 µg/ml while maintenance was at 50 µg/ml. Selection and maintenance of the survival plasmid was also carried out in HAT medium (100 µM hypoxanthine, 0.4 µM aminopterin, 16 µM thymidine; Littlefield, J. W. Science 145, 709 (1964)). GATA medium was DMEM with 10% dialyzed FCS, plus 3.5 µM guanine-HCl, 0.4 µM aminopterin, 16 µM thymidine and 35 µM adenine.

HATA medium was HAT medium plus 60 µm adenine. Concentrations of adenine were determined empirically by plating Clone 12 cells into 96 well microplates in either HAT or GAT medium with varying concentrations of adenine. Loss of survival plasmid was followed on a microplate fluorescence reader and the concentration that was not toxic and allowed a rate of plasmid loss similar to spontaneous rates was chosen.

Induction of synthetic lethality in Clone 12 cells using GSE libraries was carried out as follows. The appropriate library in either pREP9zeo or pREP9puro was transfected into cells on 35 mm plates using LIPOFECTAMINE PLUS (Life Technologies) according to manufacturer's instructions. Cells were trypsinized after 48 hours and seeded into 96 well microplates at a predetermined amount such that one colony or less would be established per well. In our hands, 1 µg of DNA gave 4000 colonies per 35 mm plate of 80% confluent cells. Seeding was in DMEM with $10^4$ non-transfected HT1080 cells per well. The appropriate selective drug in either HATA or GATA was added after another 24 hours. Selection for the libraries was at 750 µg/ml zeocin for pREP9zeo or 0.5 µg/ml puromycin for pREP9puro. Maintenance was at 400 µg/ml zeocin or 0.2 µg/ml puromycin, respectively.

D. Fluorescent Scanning of Microtiter Plates

For fluorescent scanning, cells were trypsinized and distributed at 30,000 cells/well into 96 well microplates (TPP). Growth medium was changed twice a week and plates were grown for up to 75 days. Although cell populations were very dynamic due to shedding of large clumps, almost all wells contained viable, growing cells for the entire span of the experiment. Plates were prepared for scanning by replacement of medium in wells with Hank's balanced salt solution without phenol red. This procedure minimized background fluorescence from the growth medium while maintaining maximal viability. Plates were scanned with an FL600 microplate fluorescence reader using the KC4 software (Biotek Instruments). Excitation for sphGFP was at 380 nm with a bandpass of 20 nm, while emission was measured at 508 nm with a bandpass of 40 nm. Excitation of tpzGFP was at 495 nm with a bandpass of 20 nm, while emission was measured at 535 nm with a bandpass of 40 nm. To avoid possible artifacts, all wells within a given experiment were assayed for the fluorescence of the two GFP mutants using fixed sensitivities.

Integrated sphGFP was used as an internal control for the number of cells. This was achieved by dividing the relative fluorescence resulting from the episomal tpzGFP vector by the relative fluorescence for sphGFP for each well. This ratio was then divided by the average fluorescence ratio for cells maintained under hygromycin B or HAT selection, resulting in a value representing percent remaining fluorescence for each well as compared to wells maintained under continuous selection. The data points are an average for all wells and the calculated standard deviation. Cells were returned to growth medium immediately following scanning.

E. FACS Enrichment for tpzGFP Expressing Cells

Cells transfected with the GMP synthetase GSE library were continuously grown in GATA plus 400 µg/ml zeocin in 100 mm plates and the population was expanded.. Expression of tpzGFP was followed during this time period by trypsinizing cells, several washes in PBS, resuspension in Hank's balanced salt solution and analysis of fluorescence on a FACSort (Becton Dickinson) using a 488 nm laser. After a period of three weeks following transfection, 12% of the cells retained high levels of tpzGFP, while the remaining cells lost most or all fluorescence. The highly fluorescent cells were sorted and reseeded at one cell or less per well into 96 well microplates together with $10^4$ non-transfected HT1080 cells. When colonies became apparent, microplates were read on a microplate fluorescence reader.

EXAMPLES

I. Establishment of a Model System

In order to develop a synthetic lethality screening method in human cells, Epstein-Barr virus (EBV) based episomal vectors, which can replicate autonomously as a low copy number episome in human cells of diverse tissues, were selected as the basis for the survival plasmid (J. L. Yates, N. Warren and B. Sugden, Nature 313, 812 (1985); U.S. Pat. No. 4,686,186, whose contents are incorporated herein). However, this vector is an imperfect episome because its retention in human cells requires continued selection for a dominant selectable marker gene built into the vector (D. Reisman, J. Yates and B. Sugden, Mol. Cell. Biol. 5, 1822 (1985).M. P. Calos, Trends *Genetics* 12, 463 (1996)). In the design of the system for human cells, advantage was taken of this spontaneous gradual plasmid loss, by creating synthetic lethal conditions under which retention of the episomal plasmid is essential for viability.

Figure 1:
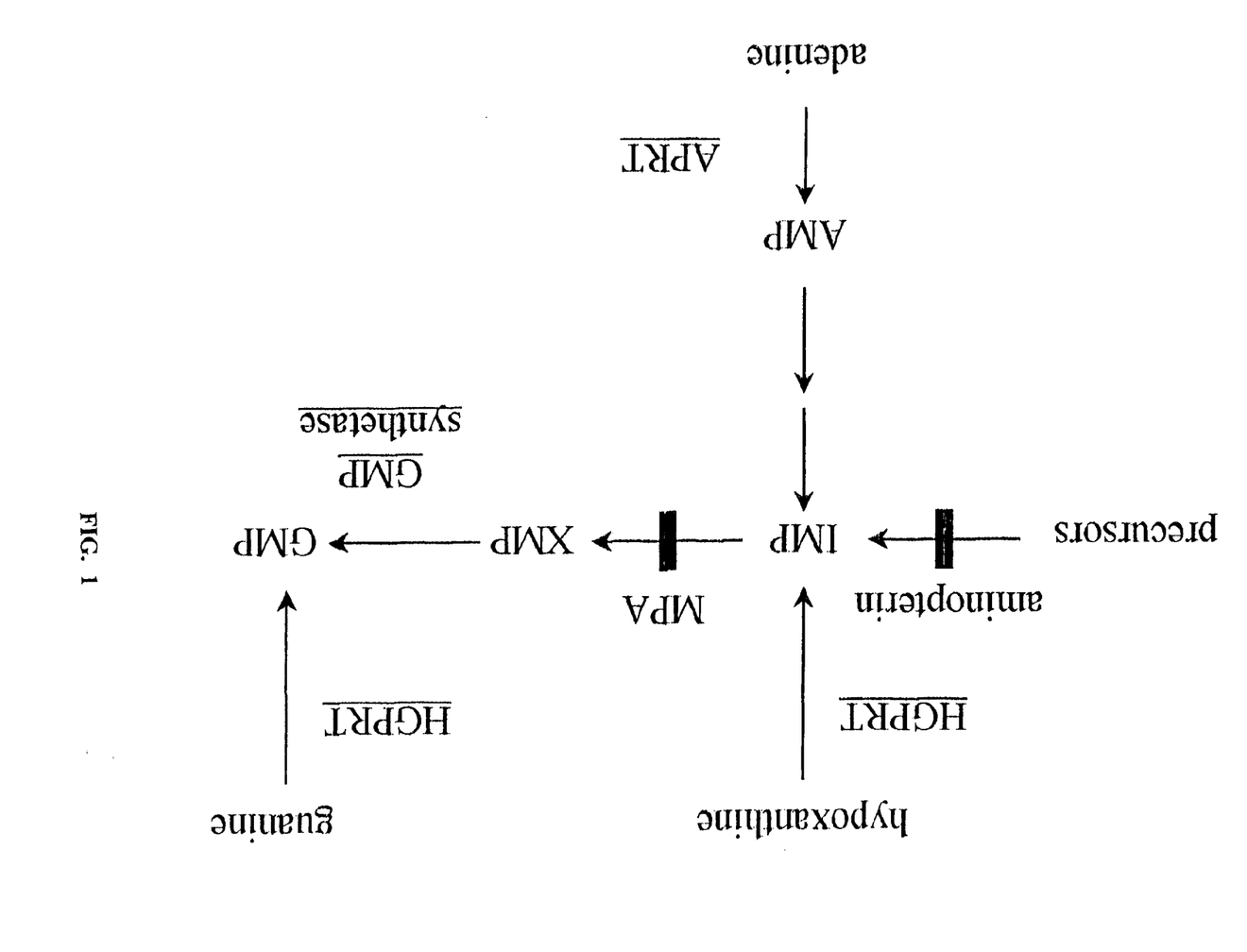
FIG. 1 illustrates de novo and salvage pathways of purine biosynthesis. Arrows indicate the action of enzymes. The sites of inhibition by mycophenolic acid (MPA) and aminopterin are marked.

As a model system for the establishment of the method, the biosynthetic pathway leading to the production of guanosine monophosphate (GMP) was chosen (FIG. 1). This pathway has been thoroughly studied biochemically and is particularly amenable to a synthetic lethality screen. First of all, the gene of interest in the model system, hypoxanthine-guanine phosphoribosyltransferase (HGPRT), is non-essential for cell survival, since it works in salvage pathways by converting hypoxanthine and guanine to IMP and GMP, respectively. Secondly, immortalized HGPRT-deficient human cell lines are available. Also, a major advantage of this model system is that de novo GMP synthesis can be specifically blocked by certain chemical reagents (FIG. 1). Accordingly, the HGPRT deficient human cells should become dependent on the HGPRT expressing "survival plasmid", when the de novo pathway is blocked by aminopterin or mycophenolic acid (MPA), in the presence of the HGPRT precursors hypoxanthine and guanine, respectively (Littlefield, op.cit.).

II. Stable Transfection of an Internal Control Fluorescent Marker

Figure 2:
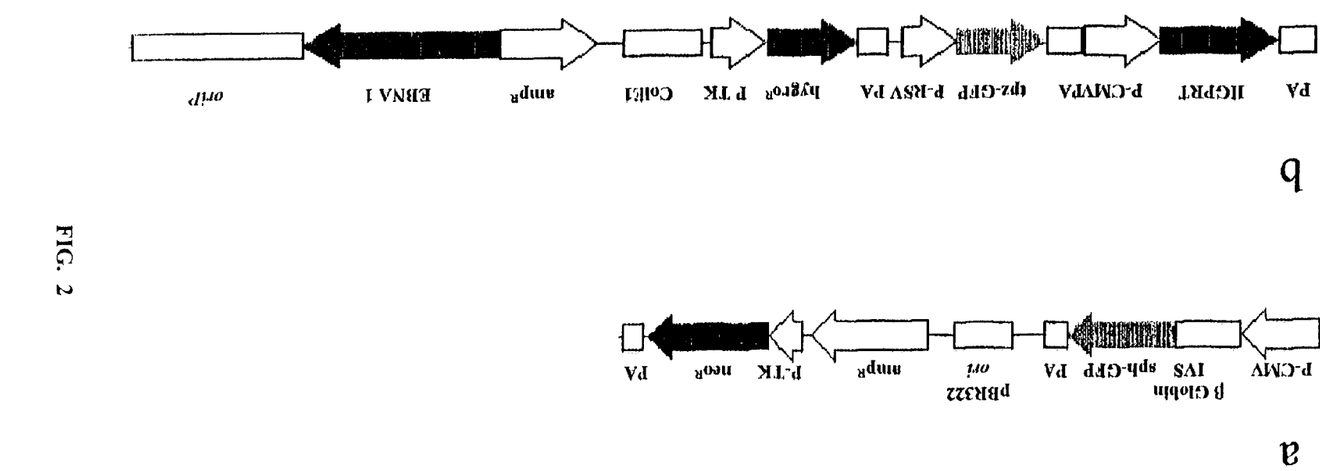
FIG. 2 illustrates the structure and expression of the double labeled GFP plasmid system.

In order to establish synthetic lethality as a high throughput screening system based on fluorescent readout, it is essential to have an internal fluorescent reporter which normalizes the fluorescent reading from the episomal survival plasmid, relative to cell number. To this end, the sapphire-blue green fluorescent protein (sphGFP), a mutant form of the natural GFP from the jellyfish *Aequara Victoria*, was chosen (U.S. Pat. No. 5,625,048, the contents of which are incorporated herein). The sphGFP coding region was cloned into a transcription unit driven by the strong CMV immediate-early promoter (U.S. Pat. No. 5,168,062, the contents of which are incorporated herein), and situated upstream of a $neo^R$ transcription unit, thus creating the vector pIS (FIG. 2a). As a recipient cell line the HGPRT-deficient variant of the HT1080 fibrosarcoma cell line was chosen (W. F. Benedict, B. E. Weissman, C. Mark and E. J. Stanbridge, Cancer Res. 44, 3471 (1984).

The pIS vector was transfected into these cells, stable clones were selected in G418, and examined with a fluorescent microscope. Clones with >99% fluorescing cells were chosen for further examination (FIG. 3). These were seeded into 96-well microplates, and scanned for fluorescence intensity using a microplate fluorescent reader, as described in the Methods section. Compared to the recipient cells, or medium alone, up to 38-fold fluorescence enhancement was recorded for the sphGFP transformants (data not shown). As expected, in the linear range of sphGFP reading, a close correlation was seen between the number of cells and the fluorescent intensity. The fluorescent intensity of these cells did not vary appreciably when removed from continuous G418 selection. Thus, the fluorescence levels obtained from the stably integrated sphGFP mutant gene are appreciable and can be easily detected as a mass population by a fluorescent microplate reader.

III. Generation of Stable Transfectants Harboring the Episomal Survival Plasmid

Survival plasmids containing a transcription unit for the human HGPRT cDNA (gene of interest) and a second GFP mutant gene, were constructed onto the backbone of the EBV-based pCEP4/pREP4 episomal vectors (FIG. 2b), as described in the Methods section. These vectors replicate autonomously as episomes in human cells due to the EBV-oriP and EBNA-1 elements (J. L. Yates, N. Warren and B. Sugden, Nature 313, 812 (1985)). They also contain the hygromycin phosphotransferase dominant selectable marker, the bacterial colE1 origin of DNA replication and the β lactamase gene.

In order to identify the survival plasmid, a second GFP variant was incorporated, the topaz-green GFP mutant gene (tpzGFP), whose expression can be distinguished from the sphGFP mutant. TpzGFP has an excitation peak (514 nm) which does not overlap with that of sphGFP (395 nm), allowing for double-label fluorescence measurements. The corresponding emission peaks are 527 nm for tpzGFP and 511 nm for sphGFP. TpzGFP was cloned under the influence of the RSV promoter (FIG. 2b). The human HGPRT cDNA was inserted in between the unique restriction sites HindIII and BamHI, so that it can be easily replaced by any human cDNA of interest (FIG. 2b). This construct, a HGPRT-tpzGFP survival plasmid, was introduced into one cell clone, HIS4, which displayed stable expression of the integrated sphGFP reporter. Stable clones resistant to HYGROMYCIN B were selected for further study, as described in the Methods section.

Most HYGROMYCIN B resistant clones were also resistant to HAT medium, indicating expression of the HGPRT transcription unit. Scanning by fluorescence microscopy was used to select several clones that express the tpzGFP in >99% of their cells. The fluorescence resulting from these two GFP variants, one stably integrated into the genome (sphGFP) and one episomal (tpzGFP), could be distinguished by use of two different filter blocks (FIG. 3, D and G vs. E and H). Similar numbers of these cells were then plated into 96 well microplates and scanned by a fluorescence microplate reader. This scanning revealed up to a 140-fold tpzGFP fluorescence increase over HIS4 autofluorescence (data not shown). It can therefore be concluded that the double-label fluorescence from the sphGFP and tpzGFP can be readily distinguished at both the single cell level by fluorescence microscopy, as well as at the mass culture level when grown in microplates, by a fluorescence microplate reader.

IV. Spontaneous Loss of the Survival Plasmid

It was next determined whether spontaneous loss of the survival plasmid could be detected by fluorescence measurements. It was imperative to show that in microtiter plates the expected plasmid loss occurs and could be detected. This is because an inherent feature of the proposed high throughput method is that scanning for genes or chemical reagents, that are synthetically lethal with a human gene of interest, will be performed on cell clones grown in microplate wells. The dynamics of cell division, and therefore the rate of the survival plasmid loss, could be very different in cells grown for long periods in microplates, as opposed to cells stimulated to divide by a regimen of periodic trypsinization, dilution and reseeding. Accordingly, measurement of fluorescence after removal of drug selection was carried out in cells continuously passaged in 90 mm plates as well as in cells grown in microtiter plates.

Figure 4:
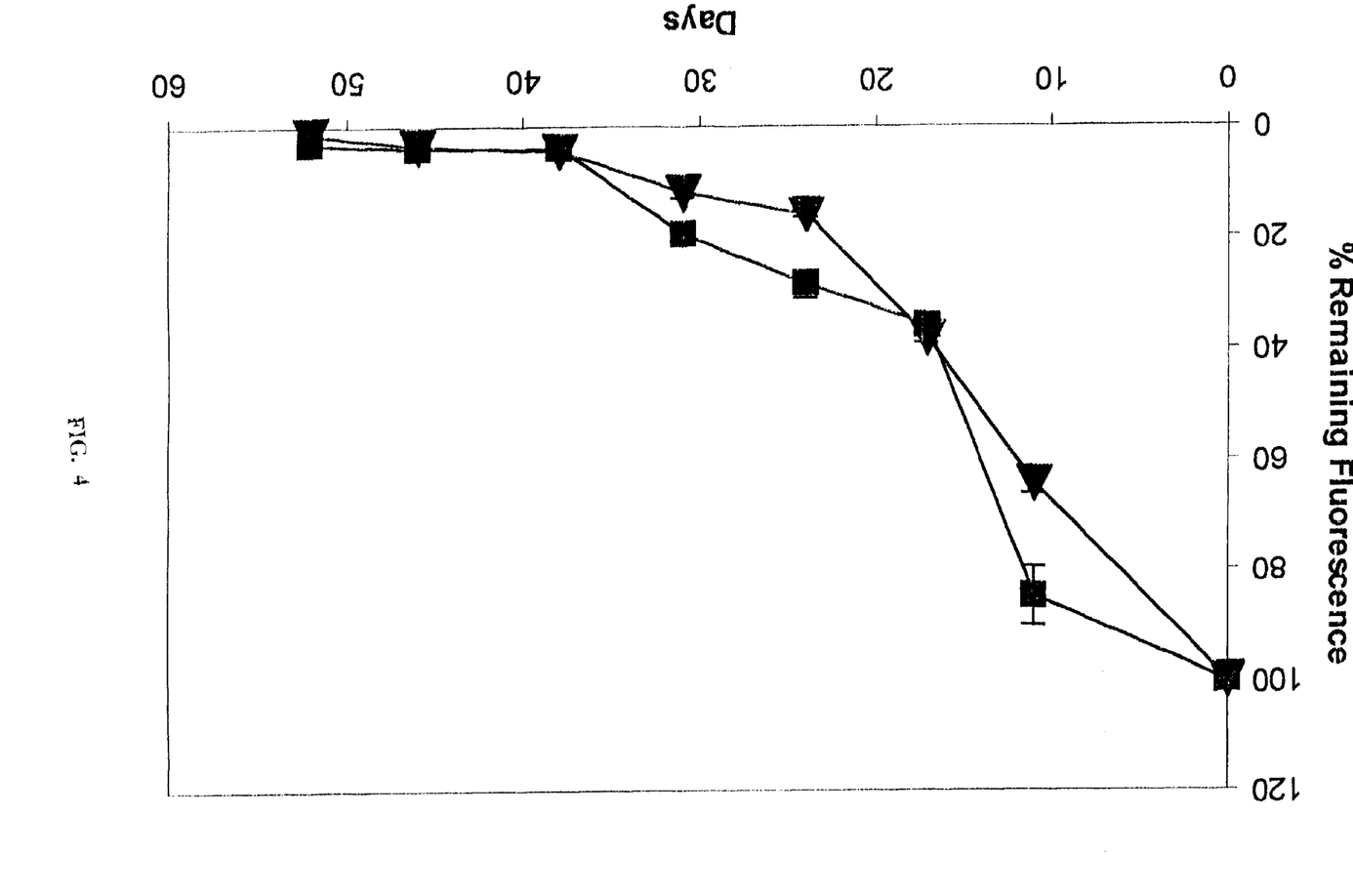
FIG. 4 shows spontaneous loss of tpzGFP-marked survival plasmid in Clone 12 cells.

Results from one isolate, Clone 12, carrying an integrated sphGFP gene and an episome-encoded tpzGFP are shown in FIG. 4. Following removal of hygromycin B from the medium, the tpzGFP and sphGFP fluorescence ratios were monitored over time. The calculated ratio was normalized to readings taken at the same time point from cells kept continuously under HYGROMYCIN B selection. As shown in FIG. 4, fluorescence from the survival plasmid marked with tpzGFP decayed rather quickly, so that after about one month, Clone 12 lost 80–90% of its initial fluorescence. Importantly, no significant difference in the rate of fluorescence decay could be detected between the cells maintained in microplate wells as opposed to those maintained by continuous passaging in petri dishes (FIG. 4). Assuming that one of the major factors affecting EBV-based plasmid loss is the rate of cell division, it could be that besides the multilayer growth of these transformed cells, the cell shedding which was observed in the microplate wells may also contribute to the dynamics of cell division.

To test whether the gradual loss of tpzGFP fluorescence over time indeed reflects the loss of survival plasmid, two assays were conducted. In one, low molecular weight DNA present in Hirt supernatants (B. Hirt, J. Mol. Biol. 26, 365 (1967) of Clone 12 cells was collected at various times after removal from hygromycin B selection. This DNA was used for bacterial transformation. It was found that the decrease of AmpR colonies correlated well with the loss of tpzGFP fluorescence over time (Table 1). In the second assay, a plasmid segregation assay (D. Reisman, J. Yates and B. Sugden, *Mol. Cell. Biol.* 5, 1822 (1985) was carried out. At each time point after drug removal, cells were reseeded into petri dishes containing hygromycin B. It was found that the number of colonies able to grow in the presence of hygromycin B, did indeed decrease at later time points (data not shown).

TABLE 1

Monitoring of spontaneous survival plasmid loss by Hirt supernatant mediated bacterial transformation.
Clone 12 cells were plated at the beginning of the experiment in DMEM without hygromycin B. Cells were continuously passaged throughout the entire experiment. Low-molecular weight DNA present in Hirt supernatants was collected at the indicated time points. All Hirt supernatants were normalized by addition of 1 ng of a chloramphenicol-resistant plasmid prior to the beginning of cell extraction. Each Hirt supernatant transformation of bacteria was plated both on chloramphenicol and ampicillin plates. Values in table were normalized to the number of colonies counted on the chloramphenicol plates.

| Days without selection | Bacterial transformants per $10^6$ Clone 12 cells | Plasmid loss (k) per day (%)* |
|---|---|---|
| 0 | 628 | |
| 21 | 38 | 13.4 |
| 25 | 23 | 13.2 |
| 38 | 16 | 9.7 |
| 46 | 0 | |

*Calculated according to 2.303 log $(N_0/N)$ = kT, where $N_0$ = % $AmP^R$ colonies at time zero (100%), N = % $AmP^R$ colonies remaining after propagation for T days without hygromycin B selection and k = % loss of plasmid per day.

V. Detection of Chemical Reagent Induced Synthetic Lethality

These results demonstrated that, in the absence of selection, the HGPRT-tpzGFP survival plasmid is unstable in HGPRT-deficient HT1080 cells. Its loss or retention can be determined by measuring its normalized florescence in a microplate reader. It was then necessary to test whether these features would enable the tracing of a synthetic lethality condition.

Figure 6:
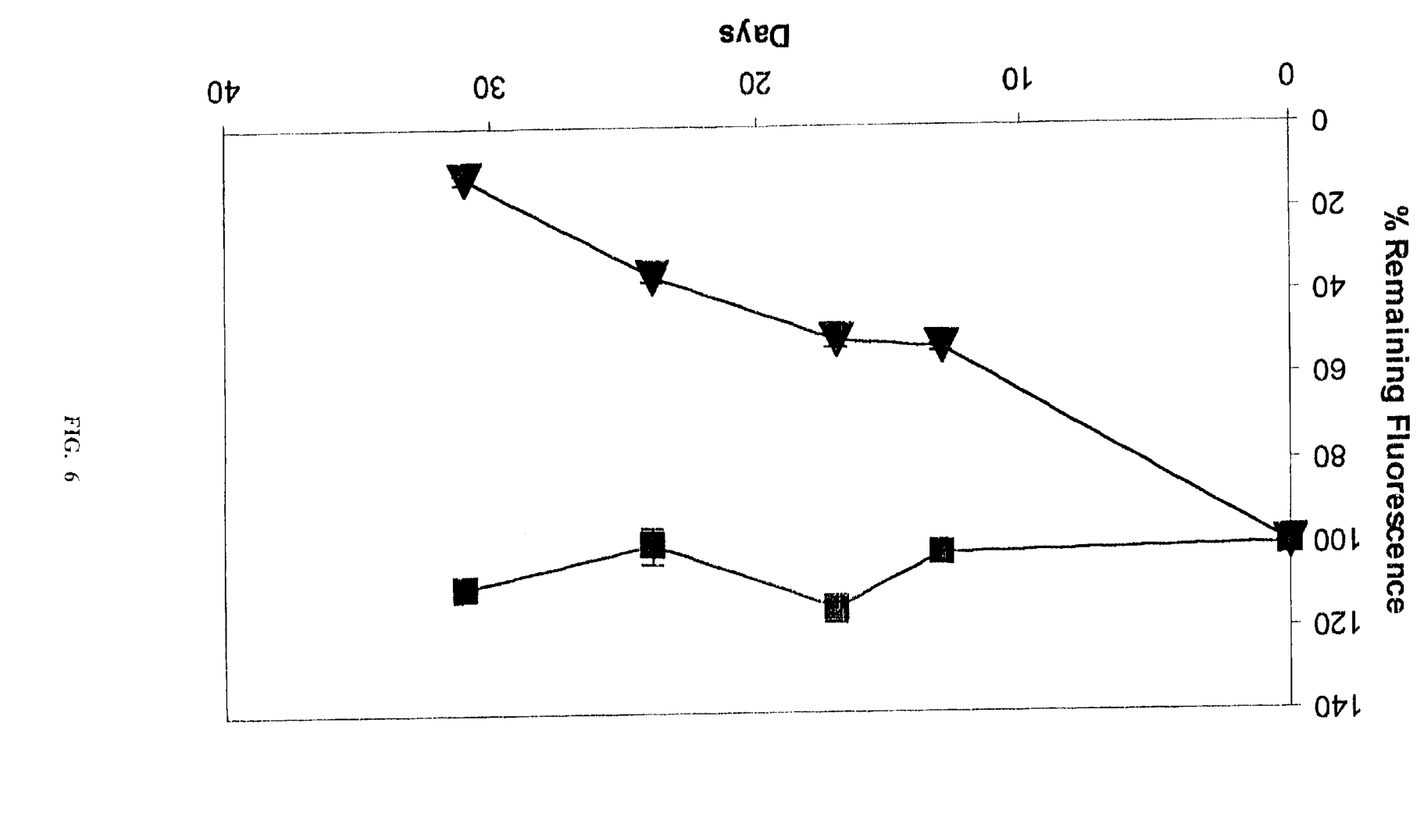

The biosynthesis of GMP from IMP via XMP can be efficiently blocked using MPA, which inhibits IMP dehydrogenase (FIG. 1). Under these conditions, normal HGPRT-positive cells can use supplied guanine to produce GMP via the salvage pathway, and survive, while HGPRT-deficient cells die. Clone 12, as an inherently HGPRT-deficient cell line, must retain the HGPRT-tpzGFP survival plasmid in order to remain alive in this synthetic lethality situation. Indeed, when HYGROMYCIN B was removed from Clone 12 cells grown in GATA medium (medium supplemented with guanine, aminopterin, thymidine and adenine—see Methods section), spontaneous loss over time of the survival plasmid occurred, as traced by a decrease in tpzGFP fluorescence (FIG. 6).

Figure 5:
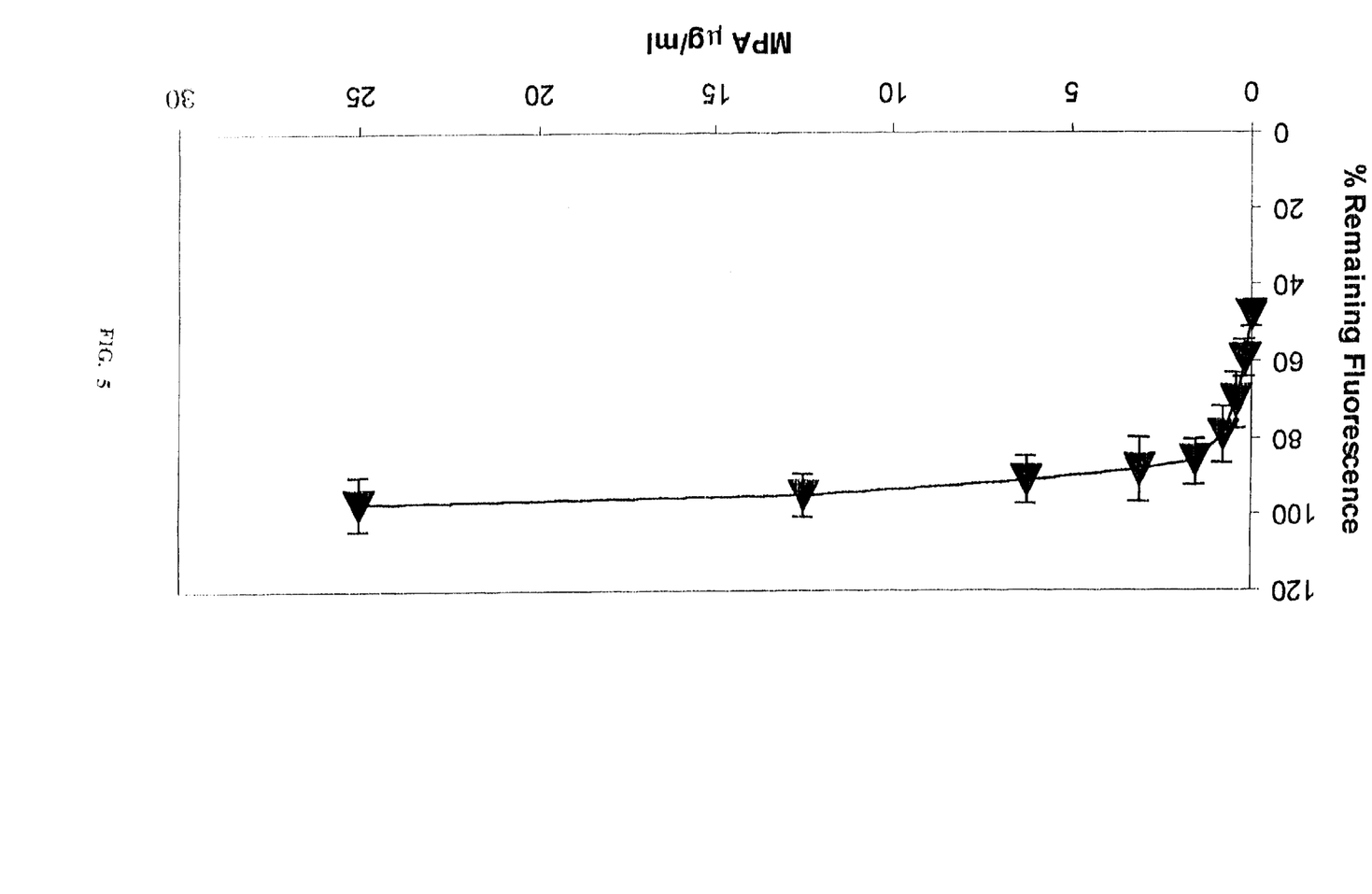
FIGS. 5 & 6 shows that synthetic lethality imposed by MPA causes retention of the survival plasmid.

It has been shown that under the specific conditions used, this loss is enabled due to a relative surplus of adenine, which besides serving as a precursor for AMP biosynthesis, allows GMP to be synthesized via the AMP-IMP-XMP pathway (data not shown, and see also Methods and FIG. 1). In contrast, addition of MPA to the GATA medium at successively higher concentrations, caused increasing retention of the survival plasmid, which could be detected by an increase in tpzGFP to sphGFP fluorescence ratio. A dose response was observed which reached a plateau at fluorescence levels similar to those obtained when HAT selection is imposed (FIG. 5). Moreover, as shown in FIG. 6, when fluorescence was observed over time, MPA could cause retention of the survival plasmid for the entire time period, while cells without MPA continued to lose tpzGFP fluorescence. Importantly, almost identical patterns of decay or retention in the presence of MPA were found when cells were grown in medium plus 3 µM guanine, without aminopterin or adenine (data not shown).

These results demonstrate the feasibility of a synthetic lethality screen in cultured human cells, using a sensitive fluorescent assay allowing detection of synthetic lethality imposed with a chemical reagent.

Figure 7:
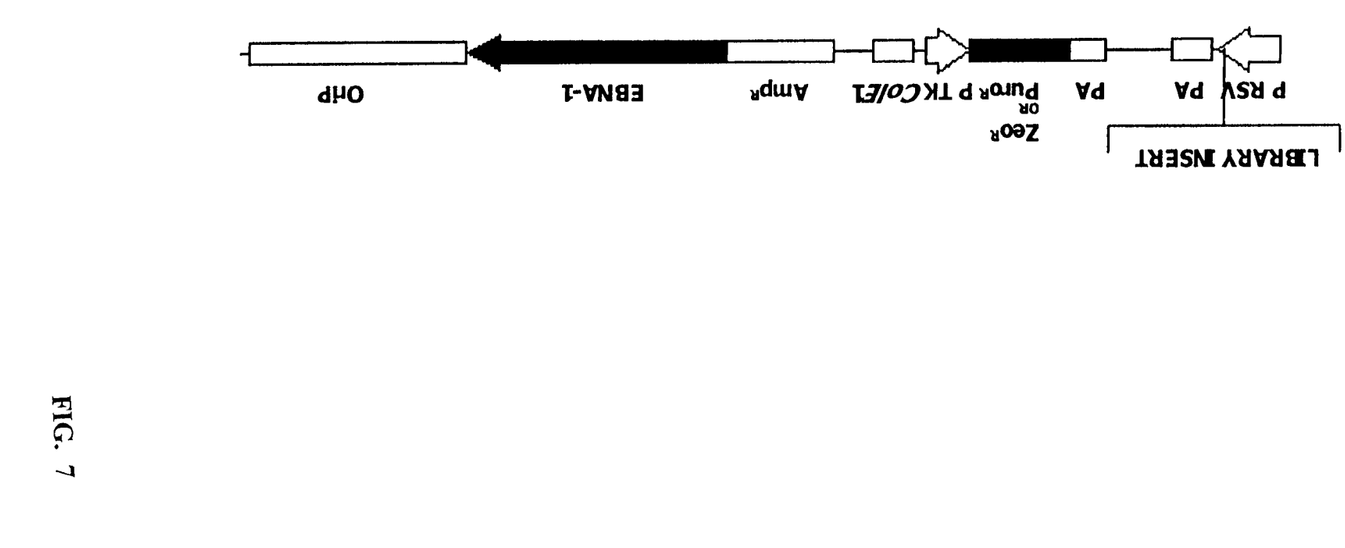
FIG. 7 illustrates the structure of the episomal GSE library plasmid.

VI Detection of Synthetic Lethality Imposed By Human APRT and GMP Synthetase—GSE libraries In order to genetically disrupt the activity of human genes in a random fashion, and then use the synthetic lethality screen to identify those genes which are synthetically lethal with the gene of interest, the GSE methodology was employed (L. P. Deiss and A. Kimchi, Science 252, 117 (1991); A. V. Gudkov et al., Proc. Natl. Acad. Sci, U.S.A. 90, 3231 (1993); V. S. Ossovskaya et al., Proc. Natl. Acad. Sci., U.S.A. 93, 10309 (1996)). The essence of this method is the generation of short truncated cDNAs or antisense cDNAs whose expression acts, at a variable frequency, in a dominant negative fashion within the transfected host cells. For this purpose pREP9-based human episomal vectors have been constructed carrying a unique dominant selectable marker, zeocin or puromycin resistance genes (FIG. 7).

An APRT GSE library incorporated into a zeocin-resistance containing episomal vector (see Methods for construction details) was transfected into Clone 12 cells held under selection for retention of the survival plasmid (HYGROMYCIN B resistance).

Following a three days expression period, the transfected cells were trypsinized off the petri dishes and seeded onto microplates at an estimated cell density of one transformant or less per well. The HYGROMYCIN B in the medium was replaced by zeocin in HATA medium. Zeocin selection ensures the retention of the GSE library in Clone 12 cells. Deficiency of the endogenous HGPRT gene dictates that in HAT medium, survival of Clone 12 cells is dependent on HGPRT-mediated conversion of hypoxanthine to IMP, with the HGPRT being encoded by the survival plasmid. Addition of 60 $\mu$M adenine to HAT (HATA medium) diverts the synthesis of GMP as well as AMP from the HGPRT-dependent salvage pathway, to the APRT-mediated conversion of adenine to AMP followed by the IMP-XMP-GMP pathway. This diversion results in the spontaneous loss of the survival plasmid in Clone 12 cells (see Methods section). However, incapacitation of APRT activity by a GSE should result in retention of the survival plasmid, because its HGPRT-encoded activity becomes essential for viability. The GSE library transfected Clone 12 cells were read periodically while in microplates, for the tpzGFP to sphGFP double-label fluorescence ratio using a microplate fluorescence reader. After about 6–8 weeks a small number of wells retained a high tpzGFP to sphGFP fluorescence ratio, meaning retention of the survival plasmid.

Figure 8:
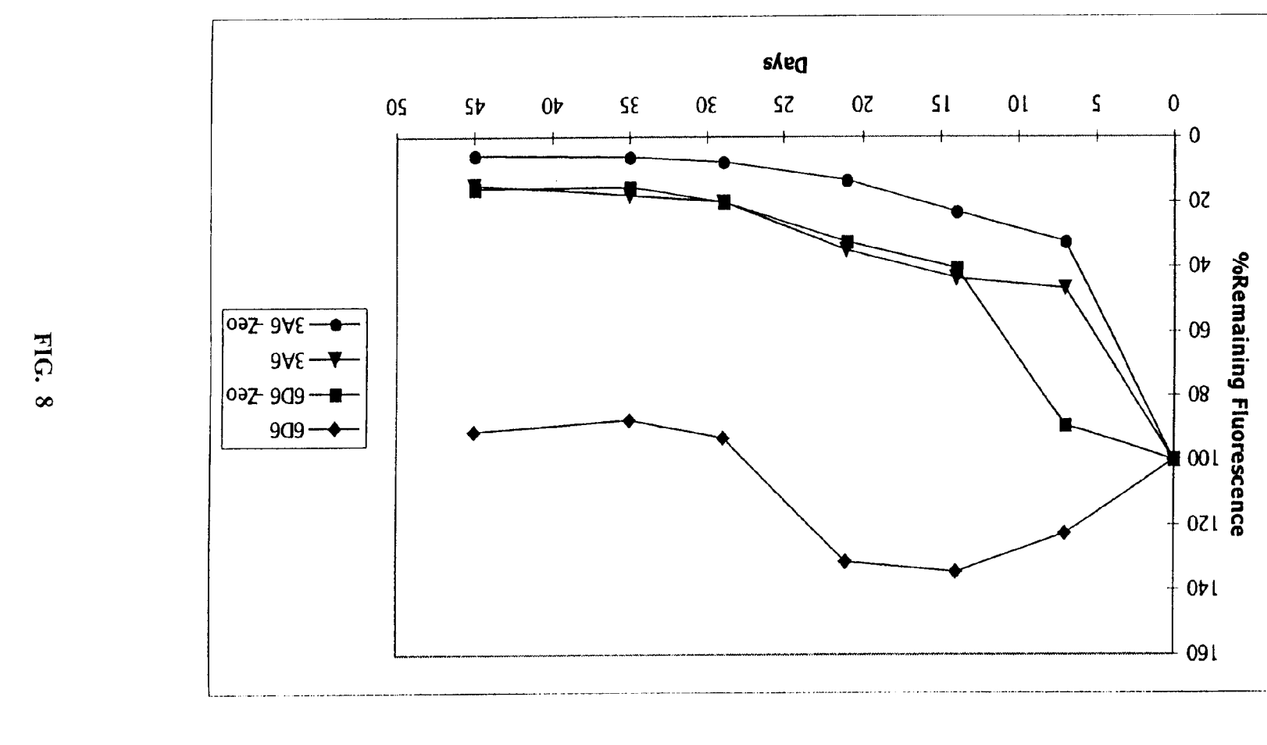
FIG. 8 shows two primary transformants of Clone 12 cells transfected with an APRT GSE library examined for retention over time of the tpzGFP fluorescence and its dependency on selection (zeocin resistance) for the GSE vector. 6D6 cells apparently contain a GSE, while 3A6 cells do not.

If retention of the survival plasmid had occurred due to incapacitation of APRT enzyme activity (as opposed for example to integration of the episomal survival plasmid into the cell genome, making it immobile), then it must be dependent on the GSE-containing plasmid. The dependence of tpzGFP fluorescence on selection to zeocine resistance encoded by the GSE vector plasmid was therefore tested. Removal of zeocine selection in clone 6D6 resulted in a typical decrease of tpzGFP fluorescence. In contrast, primary transformant 3A6 did not exhibit retention of the survival plasmid even in the presence of zeocin (FIG. 8). Thus, primary transformant 6D6 is likely to contain an APRT GSE.

In order to rescue the GSE-containing episome, low-molecular weight DNA present in the Hirt supernatant fraction of fluorescing cell clones was transformed into E. coli while selecting for zeocin resistance. Structural characterization of the plasmid clones recovered from the human cell transformants revealed on the average one to four different plasmids (that is to say different inserts). To determine which of these plasmids encoded an actual GSE, individual plasmids were reintroduced into naive Clone 12 cells. Individual secondary transformant clones were tested for retention of tpzGFP fluorescence, as outlined above. A few exhibited retention of high tpzGFP fluorescence, indicating synthetic lethality relieved by HGPRT-expression from the survival plasmid. Additionally, the cDNA inserts present in several candidate GSEs were cloned into an episomal plasmid with a puromycin resistance selectable marker. Secondary transformants were generated and their characterization with respect to tpzGFP fluorescence retention followed the protocol outlined above.

The secondary transformants retaining high tpzGFP fluorescence were further characterized for:

1. dependency on continuous selection for zeocin (or puromycin) resistance. If synthetic lethality was imposed by an APRT GSE, removal of selection for zeocin (or puromycin) which results in loss of the GSE-containing episomal plasmid, should be reflected in decreased tpzGFP fluorescence.
2. conferring of sensitivity to alanosine, which blocks conversion of IMP to AMP and therefore causes dependency on APRT-mediated conversion of adenine to AMP. Transfectants with reduced APRT activity because of a GSE action, should be more sensitive to alanosine than their parent cells.

Most, if not all, of the highly tpzGFP fluorescencing secondary transformants exhibited these features and were considered as putative GSEs. This conclusion may be further strengthened, for example, by carrying out a dose response experiment of tpzGFP fluorescence versus zeocin/puromycin concentration.

The recovered plasmids may then be analyzed for the DNA sequences which make up the GSE inserts, in order to characterize the polarity, truncated sense or antisense cDNA, as well as location within the APRT cDNA.

Figure 9:
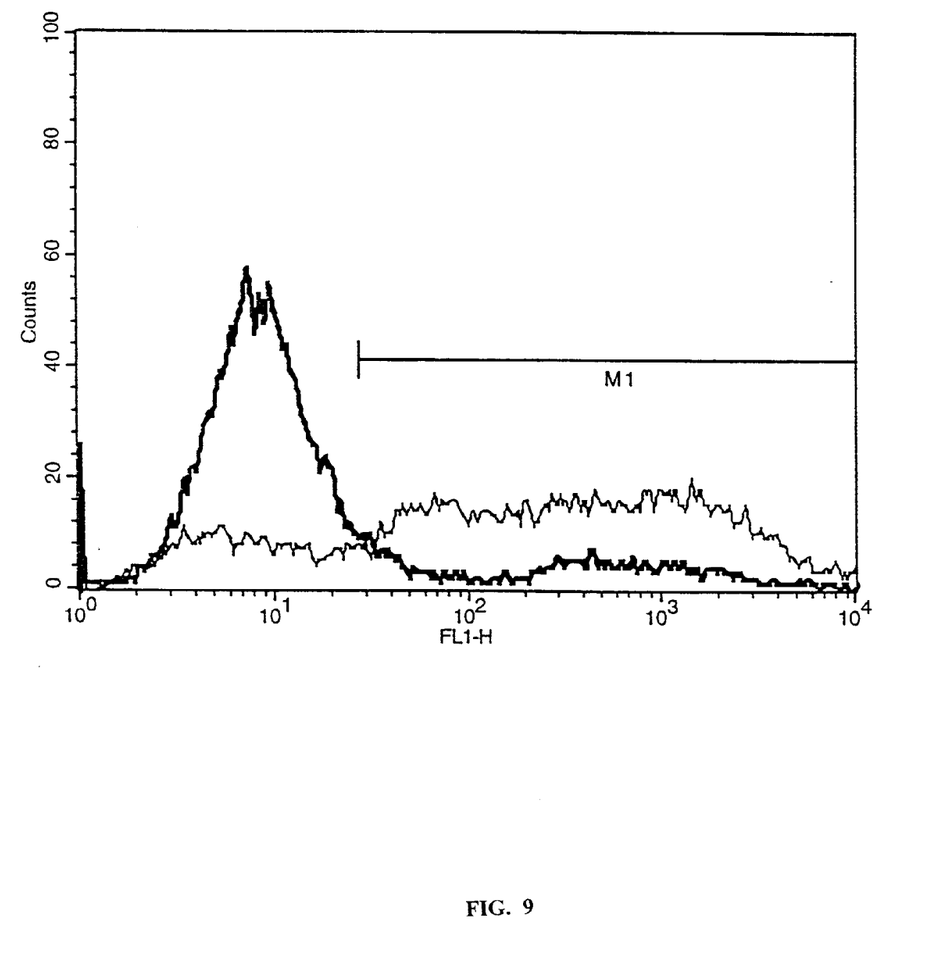
FIG. 9 shows FACS-mediated enrichment for tpzGFP-expressing cells under conditions of synthetic lethality imposed by a GSE library for human GMP synthetase. Clone 12 cells held continuously under hygromycin B selection for retention of the survival plasmid (thin line) or Clone 12 cells transfected by a human GMP synthetase GSE library (thick line) were sorted by FACS three weeks after transfection.

In a further example, the method of the invention may be utilized with respect to human GMP synthetase, albeit with one major difference. Instead of seeding GSE library transfected cells into microtiter plates soon after transfection, the cells are maintained in large petri dishes or spinner flasks for non-adherent cells for three weeks in GATA plus zeocin medium. They were then analyzed by FACS in comparison to Clone 12 cells maintained constitutively under HYGROMYCIN B selection. As shown in FIG. 9, the majority (78%) of Clone 12 cells exhibit high fluorescence due to retention of tpzGFP encoding survival plasmids. In contrast, Clone 12 cells transfected by the human GMP synthetase GSE library, and released for three weeks from HYGROMYCIN B selective pressure, exhibited a much smaller population (12%) of cells with high tpzGFP fluorescence. The latter population was sorted and seeded as single cells onto 96 well microplates and scanned periodically for tpzGFP to sphGFP fluorescence ratio as outlined above.

Among the highly tpzGFP fluorescent clones, several were shown to exhibit a zeocin dependent retention of the GMP synthetase cDNA-containing survival plasmid. These primary transfectants are considered to harbor putative GMP synthetase GSE/s.

In a manner similar to the monogenic GMP synthetase GSE library described above, whole genome GSE libraries may be scanned for genetically interacting genes. This entails among others, the construction of GSE libraries from, preferably, whole tissue normalized cDNA libraries [M. F. Bonaldo et al., Genome Res., 791 (1996)], as well as the FACS enrichment step outlined above.

The GSE libraries may be prepared from whole embryonal or adult tissue, as well as from particular cell lines. The genes may be expressed under normal or abnormal physiological states, including malignancy. With respect to mouse or other rodents, the GSE libraries may also be prepared from any of a number of embryonal developmental stages. The source for the GSE library may also be a previously enriched or selected cDNA library. Enrichment/selection may involve solution hybridization or prior selection via DNA chips. Ultimately, GSE libraries may be prepared from a full-length cDNA pool encompassing the complete coding potential of the organism.

High throughput fluorescent scanning of transfected cells which maintain the episomal survival plasmid is expected to reveal novel genes whose GSEs confer synthetic lethality upon the mutated gene of interest.

VII Rodent Model of Synthetic Lethality

Autonomous replication of a survival plasmid may be conferred by the polyoma virus origin of DNA replication together with the virus segment encoding the large T antigen (Z. Zhu et al., J. Virol. 51, 170 (1984); G. Carnenisch et al., Nuc. Acids Res. 24,3707 (1996)).

A DNA segment harboring the wild-type polyoma virus origin of DNA replication or its mutated enhancer PyEC F9-5 M. Vasseur et al., *J. Virol,* 43, 800 (1982) was ligated to a modified polyoma virus early region encoding the large T antigen only. The latter was excised by BclI and HincII restriction enzymes from the plasmid PyLT1 [Z. Zhu et al, (1984)], cloned into the versatile plasmid pJRD 184, and subsequently removed via a blunt-ended SpeI and BstEII cleavage. This segment was inserted in place of the Herpes EBV encoded oriP and EBNA-1 gene. This was accomplished by cleavage of the survival plasmid described in FIG. 2*b* with XbaI and BstEII restriction enzymes, followed by blunting of the 8 kb long fragment and its ligation to the polyoma derived DNA segment. The resulting survival plasmid may be used in chemical/genetic screening methods for synthetic lethal-chemicals or -mouse genes as described above with respect to human genes.

What is claimed is:

1. A method for screening a molecule, wherein said molecule is a cDNA which has a gene-specific lethal property, said method comprising the steps of:
   a. transfecting a first reporter gene into a non-yeast eukaryotic cells having a genome comprising a gene of interest which carries a non-lethal mutation;
   b. selecting clones stably expressing said first reporter gene;
   c. introducing into said cells an episomal survival plasmid comprising a functioning copy of said gene of interest, a second reporter gene, selectable marker, an origin of DNA replication and a nuclear antigen gene essential for replication of the plasmid within said cells, wherein said plasmid is spontaneously lost from said cells;
   d. growing said cells in the presence of a selection compound which selects for said selectable marker;
   e. selecting cell clones stably expressing said second reporter gene and said functioning copy of said gene of interest;
   f. incorporating said cDNA into a vector containing a second selectable marker gene;
   g. transfecting cells with the vector resulting from step f);
   h. removing selection for the first selectable marker;
   i. selecting for cells expressing the second selectable marker gene; and
   j. determining episomal survival plasmid retention in cells, thus identifying a cDNA having a mutant gene-specific synthetic lethal property.

2. The method according to claim 1, wherein said selectable marker is a dominant selectable marker.

3. The method according to claim 1, wherein said cells are human cells.

4. The method according to claim 1, wherein said cells are rodent cells.

5. The method according to claim 1, wherein the products of said reporter genes are fluorescent proteins.

6. The method according to claim 5, wherein the product of said first reporter gene has an excitation peak which differs from the excitation peak of the product of said second reporter gene.

7. The method according to claim 1, wherein said human cells are human cancer cells.

8. The method according to claim 7, wherein said gene of interest is specifically incapacitated in said human cancer cells.

9. The method according to claim 1, wherein said cDNA is full-length or partial-length/truncated cDNA, or cDNA in antisense orientation.

* * * * *